(12) United States Patent
Rao et al.

(10) Patent No.: US 7,161,049 B2
(45) Date of Patent: Jan. 9, 2007

(54) PROCESS FOR PURIFYING HYDROFLUOROPROPANES

(75) Inventors: Velliyur Nott Mallikarjuna Rao, Wilmington, DE (US); Allen C. Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 574 days.

(21) Appl. No.: 10/734,946

(22) Filed: Dec. 11, 2003

(65) Prior Publication Data

US 2004/0167366 A1    Aug. 26, 2004

Related U.S. Application Data

(60) Provisional application No. 60/433,295, filed on Dec. 13, 2002.

(51) Int. Cl.
*C07C 17/38* (2006.01)
(52) U.S. Cl. .................. 570/243; 502/185; 502/313; 502/355; 570/177
(58) Field of Classification Search ............... 570/243, 570/123, 216, 177
See application file for complete search history.

(56) References Cited

U.S. PATENT DOCUMENTS 5,001,287 A    3/1991    Fernandez et al.
5,208,396 A    5/1993    Anton
5,447,896 A    9/1995    Rao
5,463,152 A    10/1995    Rao
5,569,797 A    10/1996    Fu et al.
6,147,267 A    11/2000    Sievert et al.

*Primary Examiner*—Thurman K. Page
*Assistant Examiner*—Sudhakar Katakam
(74) *Attorney, Agent, or Firm*—James E. Shipley; Daniel M. Maloney

(57) ABSTRACT

A process is disclosed for purifying a hydrofluoropropane of undesirable $C_2$–$C_4$ olefinic and $C_1$–$C_4$ saturated chlorinated impurities, comprising the steps of: contacting a first mixture of hydrofluoropropane, olefinic impurity and saturated chlorinated impurity with hydrogen and hydrogen fluoride concurrently in the presence of a bifunctional catalyst, for example an alloy of gold and palladium supported on carbon, capable of catalyzing hydrogenation and fluorination. During the contacting step, olefinic impurity is converted to saturated hydrogenated derivative and/or saturated hydrofluorinated derivative, and saturated chlorinated impurity is converted to a saturated hydrodechlorinated derivative and/or saturated fluorinated derivative. The hydrofluoropropane thus formed is substantially free of both the olefinic and saturated chlorinated impurities and may be used as obtained or subject to further purification steps such as distillation to remove the process derivatives (e.g., hydrogenation, hydrodechlorination and hydrofluorination derivatives) from the hydrofluoropropane.

10 Claims, No Drawings

PROCESS FOR PURIFYING HYDROFLUOROPROPANES

BACKGROUND OF THE INVENTION

1. Field of the Invention

The present invention relates to a process for purifying hydrofluoropropanes of olefinic and saturated chlorinated impurities by concurrent contact with hydrogen and hydrogen fluoride in the presence of a bifunctional catalyst capable of catalyzing hydrogenation and fluorination.

2. Description of Related Art

Hydrofluoropropanes such as 1,1,1,2,3,3,3-heptafluoropropane ($CF_3CHFCF_3$, HFC-227ea), 1,1,1,3,3,3-hexafluoropropane ($CF_3CH_2CF_3$, HFC-236fa) and 1,1,1,3,3-pentafluoropropane ($CF_3CH_2CHF_2$, HFC-245fa) find application as fire extinguishants, propellants, refrigerants, blowing agents and solvents. Olefins and saturated chlorinated compounds are often present in product streams obtained from hydrofluoropropane manufacture. Removal of these undesirable impurities from hydrofluoropropanes by distillation is often difficult due to similar boiling points or the formation of azeotropes between impurities and hydrofluoropropanes. The presence of such impurities in hydrofluoropropanes is undesirable because they are frequently toxic as well as reactive resulting in unacceptable utility of such impure hydrofluoropropanes in most applications.

U.S. Pat. No. 5,463,152 discloses a process for the hydrogenolysis of a saturated halocarbon in the presence of a palladium on trivalent chrome oxide catalyst and an acid of the formula HZ (wherein Z is Cl, Br or F). U.S. Pat. No. 5,569,797 discloses a process for preparing a hydrochlorofluorocarbon essentially free of olefinic impurities by selectively hydrogenating the olefinic impurities in the presence of a supported or unsupported group VIII metal hydrogenation catalyst. U.S. Pat. No. 5,001,287 discloses a process for treating a mixture of olefinic impurity and saturated halocarbon by contacting the mixture with hydrogen in the presence of a supported or unsupported group VIII metal hydrogenation catalyst. U.S. Pat. No. 6,147,267 discloses a process for recovering a perfluorocycloalkane from a mixture comprising perfluorocycloalkane, an olefinic impurity, and optionally a saturated chlorinated impurity by contacting the mixture with hydrogen in the presence of a hydrogenation catalyst and separating the perfluorocycloalkane from the saturated impurity thereby produced. U.S. Pat. No. 5,208,396 discloses a process for producing saturated halocarbons by reacting saturated or olefinic compounds with hydrogen in the presence of iodine and hydrogen iodide.

The prior art discloses separate processes for removal of olefinic and chlorinated impurities from fluorocarbons that involve separate steps as well as disparate reaction conditions, reagents and catalysts. Such multi-step processes are resource intensive, less effective at producing fluorocarbon substantially free of such impurities and suffer yield loss leading to overall inefficient removal of such impurities. The present invention offers a less resource-intensive process that produces hydrofluoropropanes substantially free of olefinic and saturated chlorinated impurities in high yield by subjecting an impure hydrofluoropropane concurrently to hydrogenation with hydrogen and fluorination with hydrogen fluoride in the presence of a bifunctional catalyst.

BRIEF SUMMARY OF THE INVENTION

The present invention is a process for purifying a hydrofluoropropane comprising: contacting a first mixture comprising a hydrofluoropropane, an olefinic impurity and a saturated chlorinated impurity with hydrogen and hydrogen fluoride concurrently in the presence of a bifunctional catalyst, whereby said olefinic impurity is converted to at least one first saturated derivative selected from the group consisting of a saturated hydrogenated derivative of said olefinic impurity and a saturated hydrofluorinated derivative of said olefinic impurity, and whereby said saturated chlorinated impurity is converted to at least one second saturated derivative selected from the group consisting of a saturated hydrodechlorinated derivative of said saturated chlorinated impurity and a saturated fluorinated derivative of said saturated chlorinated impurity, to form a second mixture comprising hydrofluoropropane substantially free of said olefinic impurity and said saturated chlorinated impurity, and recovering said second mixture. Such purified hydrofluoropropane may be used as so obtained or may be subjected to further purification steps, such as distillation, to remove the first and second saturated derivatives from the hydrofluoropropane.

DETAILED DESCRIPTION OF THE INVENTION

Hydrofluoropropanes of the present invention are represented by the formula $C_3H_mF_{8-m}$, wherein m is an integer from 1 to 7. Representative hydrofluoropropanes include:

1,1,1,2,3,3,3-heptafluoropropane ($CF_3CHFCF_3$, HFC-227ea), 1,1,1,2,2,3,3-heptafluoropropane ($CF_3CF_2CHF_2$, HFC-227ca),
1,1,1,3,3,3-hexafluoropropane ($CF_3CH_2CF_3$, HFC-236fa),
1,1,1,2,3,3-hexafluoropropane ($CF_3CHFCHF_2$, HFC-236ea),
1,1,1,2,2,3-hexafluoropropane ($CF_3CF_2CH_2F$, HFC-236cb),
1,1,1,3,3-pentafluoropropane ($CF_3CH_2CHF_2$, HFC-245fa),
1,1,2,3,3-pentafluoropropane ($CHF_2CHFCHF_2$, HFC-245ea),
1,1,1,2,3-pentafluoropropane ($CF_3CHFCH_2F$, HFC-245eb),
1,1,1,2,2-pentafluoropropane ($CF_3CF_2CH_3$, HFC-245cb),
1,1,2,2,3-pentafluoropropane ($CHF_2CF_2CH_2F$, HFC-245ca),
1,1,2,2-tetrafluoropropane ($CHF_2CF_2CH_3$, HFC-254cb),
1,1,3,3-tetrafluoropropane ($CHF_2CH_2CHF_2$, HFC-254fa),
1,1,1,3-tetrafluoropropane ($CF_3CH_2CH_2F$, HFC-254fb),
1,2,2-trifluoropropane ($CH_2FCF_2CH_3$, HFC-263ca), 1,1,1-trifluoropropane ($CF_3CH_2CH_3$, HFC-263fb), 2,2-difluoropropane ($CH_3CF_2CH_3$, HFC-272ca), 1,1-difluoropropane ($CHF_2CH_2CH_3$, HFC-272fb), and 2-fluoropropane ($CH_3CHFCH_3$, HFC-281ea).

Hydrofluoropropanes of the present invention are known compounds that may be prepared by various processes such as addition of HF to haloolefins or exchange of chlorine substituents in saturated halopropanes for fluorine by the action of HF in the presence of a catalyst. Examples of such hydrofluoropropane manufacturing processes include: the addition of HF to hexafluoropropene to give HFC-227ea as disclosed in U.S. Pat. No. 6,281,395; the addition of HF to 1,1,3,3,3-pentafluoro-1-propene to give HFC-236fa and the addition of HF to 1,2,3,3,3-pentafluoro-1-propene to give HFC-236ea as disclosed in U.S. Pat. No. 5,563,304; the addition of HF to 1-chloro-3,3,3-trifluoro-1-propene to give HFC-245fa as disclosed in U.S. Pat. No. 6,063,970; the addition of HF to 1,3,3,3-tetrafluoro-1-propene to give HFC- 245fa as disclosed in U.S. Pat. No. 6,111,150; the addition of HF to 2-chloropropene as disclosed in Great Britain Patent No. 1,006,456; the addition of HF to propene as reported by Gross and Lin in *Journal of Organic Chemistry*, Volume 3, pp. 26 to 32 (1938); the reaction of 1,1,1,3,3,3-hexachloropropane with HF to give HFC-236fa as disclosed in U.S. Pat. Nos. 5,414,165 and 5,545,774; the reaction of 1,1,1,3,3-pentachloropropane with HF to give HFC-245fa as disclosed in U.S. Pat. No. 6,291,730; and the reaction of a mixture of 1,1,1,3,3,3-hexachloropropane and 1,1,1,3,3-pentachloropropane with HF to give a mixture of HFC-236fa and HFC-245fa as disclosed in U.S. Pat. No. 5,763,706.

The process of the present invention is particularly suitable for purifying hydrofluoropropanes obtained from such manufacturing processes as azeotropes with hydrogen fluoride. Examples of hydrofluoropropanes which may be obtained as azeotropes with hydrogen fluoride include HFC-227ea, HFC-236ea, HFC-236fa and HFC-245fa, as disclosed in U.S. Pat. Nos. 6,376,727, 5,563,304, and 6,291,730.

Olefinic impurities of the present invention are represented by the formula $C_nH_pCl_qF_r$, wherein n is an integer from 2 to 4, p is an integer from 0 to 8, q is an integer from 0 to 2, r is an integer from 0 to 8, and p+q+r=2n. Representative olefinic impurities of the present invention include: hexafluoropropene ($CF_3CF=CF_2$, HFP); 2-chloro-1,1,3,3,3-pentafluoro-1-propene ($CF_3CCl=CF_2$, CFC-1215xc); 1,1,3,3,3-pentafluoro-1-propene ($CF_3CH=CF_2$, HFC-1225zc); E- and Z-1,2,3,3,3-pentafluoro-1-propene ($CF_3CF=CHF$, HFC-1225ye); E- and Z-1-chloro-1,3,3,3-tetrafluoro-1-propene ($CF_3CH=CClF$, HCFC-1224zb); E- and Z-1,2-dichloro-3,3,3-trifluoro-1-propene ($CF_3CCl=CHCl$, HCFC-1223xd); 1,1-dichloro-3,3,3-trifluoro-1-propene ($CF_3CH=CCl_2$, HCFC-1223za); E- and Z-1,3,3,3-tetrafluoro-1-propene ($CF_3CH=CHF$, HFC-1234ze); 2,3,3,3-tetrafluoro-1-propene ($CF_3CF=CH_2$, HFC-1234yf); E- and Z-1-chloro-3,3,3-trifluoro-1-propene ($CF_3CH=CHCl$, HCFC-1233zd); 2-chloro-3,3,3-trifluoro-1-propene ($CF_3CCl=CH_2$, HCFC-1233xf); 3,3,3-trifluoro-1-propene ($CF_3CH=CH_2$, HFC-1243zf); 2-fluoropropene ($CH_3CF=CH_2$, HFC-1261yf); propene ($C_3H_6$); E- and Z-octafluoro-2-butene ($CF_3CF=CFCF_3$, FC-1318myy); E- and Z-1,1,1,2,4,4,4-heptafluoro-2-butene ($CF_3CF=CHCF_3$, HFC-1327myz); E- and Z-2-chloro-1,1,1,3,3,3-hexafluoro-2-butene ($CF_3CCl=CHCF_3$, HCFC-1326mxz); E- and Z-1,1,1,4,4,4-hexafluoro-2-butene ($CF_3CH=CHCF_3$, HFC-1336mzz); 1,1-dichloro-2,2-difluoroethene ($CF_2=CCl_2$, CFC-1112a); and 1,1-difluoroethene ($CF_2=CH_2$, vinylidene fluoride).

Saturated chlorinated impurities of the present invention are represented by the formula $C_sH_tCl_uF_v$, wherein s is an integer from 1 to 4, t is an integer from 0 to 9, u is an integer from 1 to 3, v is an integer from 0 to 9, and t+u+v=2s+2. Representative saturated chlorinated impurities of the present invention include chlorofluorocarbons (e.g., chlorofluoromethanes, chlorofluoroethanes and chlorofluoropropanes), hydrochlorofluorocarbons (e.g., hydrochlorofluoromethanes, hydrochlorofluoroethanes, hydrochlorofluoropropanes and hydrochlorofluorobutanes), and chlorocarbons and hydrochlorocarbons (e.g., (hydro)chloromethanes, (hydro)chloroethanes and (hydro)chloropropanes), specific examples including, $CH_2Cl_2$, $CHCIF_2$, $CClF_3$, $CCl_2F_2$, $CHClFCF_3$, $CF_3CH_2CHClF$, $CF_3CHClCF_3$, $CF_3CCl_2CF_3$, $CF_3CHClCHF_2$, $CF_3CH_2CClF_2$, and $CF_3CHClCClF_2$.

The contacting step of the present process is performed in the presence of a bifunctional catalyst capable of catalyzing both hydrogenation and fluorine-for-chlorine halogen exchange fluorination reactions. Hydrogenation refers to the bifunctional catalyst's ability to catalyze addition of hydrogen across a carbon-carbon double bond of an olefinic impurity (e.g., the basic process C=C+$H_2$—>H—C—C—H), as well as the catalyst's ability to catalyze hydrodechlorination of a carbon-chlorine bond in a saturated chlorinated impurity resulting in formation of a carbon-hydrogen bond in place of the carbon-chlorine bond (e.g., the basic process C—Cl+$H_2$—>C—H). Fluorination refers to the bifunctional catalyst's ability to catalyze the addition of hydrogen fluoride across the carbon-carbon double bond of an olefinic impurity (e.g., the basic process C=C+HF—>H—C—C—F), as well as the catalyst's ability to catalyze fluorine-for-chlorine halogen exchange fluorination of a carbon-chlorine bond in a saturated chlorinated impurity, resulting in formation of a carbon-fluorine bond in place of the carbon-chlorine bond (e.g., the basic process C—Cl+HF—>C—F).

Bifunctional catalysts of the present invention are comprised of a hydrogenating component and a fluorinating component. The hydrogenating component of the bifunctional catalyst comprises at least one of the transition metals palladium and platinum, optionally further comprising gold, and mixtures thereof. The hydrogenating component may comprise mixtures such as alloys of these metals, for instance, alloys of palladium and gold. The fluorinating component of the bifunctional catalyst comprises at least one fluorination catalyst capable of catalyzing the addition of hydrogen fluoride across carbon-carbon double bonds, or capable of catalyzing fluorine-for-chlorine halogen exchange fluorination of a carbon-chlorine bond. Representative fluorination catalysts comprise carbon, aluminum (III)-containing compounds and chromium(III)-containing compounds including: aluminum(III) oxide; fluorinated aluminum(III) oxide; chromium(III) oxide; fluorinated chromium(III) oxide; $Cr_2O_3/MgO/Al_2O_3$; $Cr(III)/AlF_3$; $Zn/Al_2O_3$; Cr, Mn Ni or Co supported on high fluorine content (greater than 90 wt % $AlF_3$) alumina; $CrCl_3$, $CoCl_2/CeCl_3$, $NiCl_2$ or $CoCl_2/MgCl_2$ supported on $\gamma$-$Al_2O_3$; and $AlCl_xF_y(x+y=3)$; as well as mixtures of such fluorination catalysts. The preferred fluorinating component of the present bifunctional catalysts are carbon, fluorinated aluminum(III) oxide, fluorinated chromium(III) oxide, or mixtures thereof. Such fluorination catalysts are generally known in this field and described, for instance, in the review "Catalytic Routes to Hydro(chloro)fluorocarbons" by Z. Ainbinder, L. E. Manzer and M. J. Nappa, chapter 1.4, found at pages 1677 through 1685 of the *Handbook of Heterogeneous Catalysis*, volume 4, edited by G. Ertl, H. Knozinger and J. Weitkamp, published by VCH Verlagsgesellschaft mbH, Weinheim (Federal Republic of Germany), ISBN 3-527-29212-8, herein incorporated by reference.

The hydrogenating component of the present bifunctional catalyst may be supported on the fluorinating component. The amount of hydrogenating component supported on the fluorinating component may be from about 0.1 weight percent to about 10 weight percent, preferably from about 0.2 weight percent to about 5 weight percent, based on the combined weight of the hydrogenating component and the fluorinating component.

Palladium on chromium oxide prepared by the procedure disclosed in U.S. Pat. No. 5,463,152, herein incorporated by reference, and palladium on fluorided alumina prepared by the procedure disclosed in U.S. Pat. No. 4,873,381, herein incorporated by reference, are bifunctional catalysts of utility in the present process. When the hydrogenation component of the bifunctional catalyst comprises an alloy of gold and palladium, it is preferably supported on a carbon fluorination component. Preferred bifunctional catalysts of the present invention comprise a hydrogenation component of palladium and/or platinum in combination with gold. For this preferred bifunctional catalyst, the amount of the gold is from about 5 to about 95 weight percent, preferably from about 20 to about 70 weight percent, of the combined weight of the gold, palladium and platinum. The preparation of such bifunctional catalysts containing palladium and gold on a carbon support is described in U.S. Pat. No. 5,447,896, herein incorporated by reference. When the fluorination component is carbon, it is preferred that the carbon be washed with acid to remove alkali metal impurities as described in U.S. Pat. No. 5,136,113, herein incorporated by reference. The most preferred bifunctional catalysts of the present invention comprise alloys of gold and palladium supported on acid-washed carbon.

The contacting step of the present process can result in addition of hydrogen across carbon-carbon double bond(s) in the olefinic impurity and conversion of the olefinic impurity to a saturated hydrogenated derivative. Representative saturated hydrogenated derivatives formed by such hydrogenation of olefinic impurities include: 1,1,1,2,3,3-hexafluoropropane ($CF_3CHFCHF_2$, HFC-236ea) formed from hexafluoropropene; 2-chloro-1,1,1,3,3-pentafluoropropane ($CF_3CHClCHF_2$, HCFC-235da) formed from 2-chloro-1,1,3,3,3-pentafluoro-1-propene; 1,1,1,3,3-pentafluoropropane ($CF_3CH_2CHF_2$, HFC-245fa) formed from 1,1,3,3,3-pentafluoro-1-propene; 1,1,1,2,3-pentafluoropropane ($CF_3CHFCH_2F$, HFC-245eb) formed from 1,1,1,2,3-pentafluoro-1-propene; 1-chloro-1,3,3,3-tetrafluoropropane ($CF_3CH_2CHClF$, HCFC-244fa) formed from E- or Z-1-chloro-1,3,3,3-tetrafluoro-1-propene; 1,2-dichloro-3,3,3-trifluoropropane ($CF_3CHClCH_2Cl$, HCFC-243 db) formed from E- or Z-1,2-dichloro-3,3,3-trifluoro-1-propene; 1,1-dichloro-3,3,3-trifluoropropane ($CF_3CH_2CHCl_2$, HCFC-243fa) formed from 1,1-dichloro-3,3,3-trifluoro-1-propene; 1,1,1,3-tetrafluoropropane ($CF_3CH_2CH_2F$, HFC-254fb) formed from E- or Z-1,3,3,3-tetrafluoro-1-propene; 1,1,1,2-tetrafluoropropane ($CF_3CHFCH_3$, HFC-254eb) formed from 2,3,3,3-tetrafluoro-1-propene; 3-chloro-1,1,1-trifluoropropane ($CF_3CH_2CH_2Cl$, HCFC-253fb) formed from E- or Z-1-chloro-3,3,3-trifluoro-1-propene; 2-chloro-1,1,1-trifluoropropane ($CF_3CHClCH_3$, HCFC-253 db) formed from 2-chloro-3,3,3-trifluoro-1-propene; 1,1,1-trifluoropropane ($CF_3CH_2CH_3$, HFC-263fb) formed from 3,3,3-trifluoro-1-propene; propane ($C_3H_8$) formed from propene; 1,1,1,2,3,4,4,4-octafluorobutane ($CF_3CHFCHFCF_3$, HFC-338mee) formed from E- or Z-octafluoro-2-butene; 1,1,1,2,4,4,4-heptafluorobutane ($CF_3CHFCH_2CF_3$, HFC-347mef) formed from E- or Z-1,1,1,2,4,4,4-heptafluoro-2-butene; 2-chloro-1,1,1,4,4,4-hexafluorobutane ($CF_3CHClCH_2CF_3$, HCFC-346mdf) formed from E- or Z-2-chloro-1,1,1,4,4,4-hexafluoro-2-butene; 1,1,1,4,4,4-hexafluorobutane ($CF_3CH_2CH_2CF_3$, HFC-356mff) formed from E- or Z-1,1,1,4,4,4-hexafluoro-2-butene; 1,1-dichloro-2,2-difluoroethane ($CHF_2CHCl_2$, HCFC-132a) formed from 1,1-dichloro-2,2-difluoroethene; and 1,1-difluoroethane ($CHF_2CH_3$, HFC-152a) formed from 1,1-difluoroethene.

The contacting step of the present process can result in the substitution of chlorine in a saturated chlorinated impurity by hydrogen and conversion of the saturated chlorinated impurity to a saturated hydrodechlorinated derivative. Representative saturated hydrodechlorinated derivatives formed by such hydrogenation of saturated chlorinated impurities include: methane from methylene chloride; difluoromethane ($CH_2F_2$, HFC-32) from chlorodifluoromethane; trifluoromethane ($CHF_3$, HFC-23) from chlorotrifluoromethane; 1,1,1-trifluoroethane ($CH_3CF_3$, HFC-143a) from 2-chloro-1,1,1-trifluoroethane; 1,1,1,2-tetrafluoroethane ($CH_2FCF_3$, HFC-134a) from 2-chloro-1,1,1,2-tetrafluoroethane; 1,1,1,3,3,3-hexafluoropropane ($CF_3CH_2CF_3$, HFC-236fa) from 2-chloro-1,1,1,3,3,3-hexafluoropropane or 2,2-dichloro-1,1,1,3,3,3-hexafluoropropane; and 1,1,1,3,3-pentafluoropropane ($CF_3CH_2CHF_2$, HFC-245fa) from 2-chloro-1,1,1,3,3-pentafluoropropane, 3-chloro-1,1,1,3,3-pentafluoropropane, or 2,3-dichloro-1,1,1,3,3-pentafluoropropane; along with HCl co-product.

Where an olefinic impurity that contains chlorine is hydrogenated to a saturated hydrogenated derivative that also contains chlorine, such compound is essentially an (in situ-formed) saturated chlorinated impurity. Such in situ-formed saturated chlorinated impurities will be further hydrogenated under the present contacting step conditions to yield a corresponding saturated hydrodechlorinated derivative. For example, hydrogenation of olefinic impurity 2-chloro-1,1,3,3,3-pentafluoro-1-propene (CFC-1215xc) gives saturated hydrogenated derivative 2-chloro-1,1,1,3,3-pentafluoropropane (HCFC-235da); also a saturated chlorinated impurity. So formed HCFC-235da will in turn be hydrogenated (hydrodechlorinated) to a saturated hydrodechlorinated derivative 1,1,1,3,3-pentafluoropropane (HFC-245fa) under the present contacting step operating conditions.

The contacting step of the present process can result in addition of hydrogen fluoride across carbon-carbon double bond(s) in an olefinic impurity and conversion of the olefinic impurity to a saturated hydrofluorinated derivative. Representative saturated hydrofluorinated derivatives include: 1,1,1,2,3,3,3-heptafluoropropane ($CF_3CHFCF_3$, HFC-227ea) from hexafluoropropene; 2,3-dichloro-1,1,1,3,3-pentafluoropropane ($CF_3CHClCClF_2$, HCFC-225da) from 2-chloro-1,1,3,3,3-pentafluoro-1-propene; 1,1,1,3,3,3-hexafluoropropane ($CF_3CH_2CF_3$, HFC-236fa) from 1,1,3,3,3-pentafluoro-1-propene; 1,1,1,2,3,3-hexafluoropropane ($CF_3CHFCHF_2$, HFC-236ea) from 1,1,1,2,3-pentafluoro-1-propene; 3-chloro-1,1,1,3,3-pentafluoropropane ($CF_3CH_2CClF_2$, HCFC-235fa) from E- or Z-1-chloro-1,3,3,3-tetrafluoro-1-propene; 3,3-dichloro-1,3,3,3-tetrafluoropropane ($CF_3CH_2CCl_2F$, HCFC-234fb) from 1,1-dichloro-3,3,3-trifluoro-1-propene; 1,1,1,3,3-pentafluoropropane ($CF_3CH_2CHF_2$, HFC-245fa) from E- or Z-1,3,3,3-tetrafluoro-1-propene; 3-chloro-1,1,1,3-tetrafluoropropane ($CF_3CH_2CHClF$, HCFC-244fa) from E- or Z-1-chloro-3,3,3-trifluoro-1-propene; 1,1,2-trichloro-2,2-difluoroethane ($CHCl_2CClF_2$, HCFC-122) and/or 1,1-dichloro-2,2,2-trifluoroethane ($CHCl_2CF_3$, HCFC-123) from 1,1-dichloro-2,2-difluoroethene; 1,1-difluoroethane ($CHF_2CH_3$, HFC-152a) from fluoroethene; and 1,1,1-trifluoroethane ($CF_3CH_3$, HFC-143a) from 1,1-difluoroethene.

The contacting step of the present process can result in substitution of chlorine in a saturated chlorinated impurity by fluorine and conversion of the saturated chlorinated impurity to a saturated fluorinated derivative. Representative saturated fluorinated derivatives include: difluoromethane ($CH_2F_2$, HFC-32) from dichloromethane; 1,1,1,3,3-pentafluoropropane ($CF_3CH_2CHF_2$, HFC-245fa) from 3-chloro-1,1,1,3-tetrafluoropropane; 1,1,1,3,3,3-hexafluoropropane ($CF_3CH_2CF_3$, HFC-236fa) from 3-chloro-1,1,1,3,3-pentafluoropropane; and 2-chloro-1,1,1,3,3,3-hexafluoropropane ($CF_3CHClCF_3$, HCFC-226da) from 2,3-dichloro-1,1,1,3,3-pentafluoropropane.

The contact time over which period the first mixture of the present invention, comprising hydrofluoropropane, olefinic impurity and saturated chlorinated impurity, is contacted with hydrogen and hydrogen fluoride concurrently in the presence of bifunctional catalyst is not critical. The contact time should be of sufficient duration such that olefinic impurity is converted to at least one first saturated derivative selected from the group consisting of a saturated hydrogenated derivative and a saturated hydrofluorinated derivative. The contact time should also be of sufficient duration such that the saturated chlorinated impurity is converted to at least one second saturated derivative selected from the group consisting of a saturated hydrodechlorinated derivative and a saturated fluorinated derivative. To obtain such conversion of such impurities, contact times may be from about 1 to about 120 seconds, preferably from about 5 to about 60 seconds.

The mole ratio of hydrogen to the total of the olefinic impurities and saturated chlorinated impurities is not critical but is typically from about 1 mole of hydrogen per mole of impurity to about 500 moles of hydrogen per mole of impurity. The ratio of hydrogen to hydrogen fluoride is not critical but is typically between about 1:10 and about 1:1, preferably between about 1:1 and about 1:4. The concentration of the impurities present in the first mixture comprising hydrofluoropropane will vary from one hydrofluoropropane or manufacturing process to another, but is typically within the range of about 50 ppm to about 100,000 ppm. Large excesses of hydrogen in the present contacting step should be avoided as this may cause difficulties in recovering hydrofluoropropane product.

The total pressure during the contacting step of the present invention is not critical. Atmospheric and superatmospheric are the most convenient and are therefore preferred.

The temperature at which the contacting step of the present process is carried out may be from about 100° C. to about 400° C., preferably from about 200° C. to about 350° C. The temperature at which at least a portion of the olefinic impurity is converted to a first saturated derivative selected from the group consisting of a saturated hydrogenated derivative and a saturated hydrofluorinated derivative may be from about 100° C. to about 250° C. The temperature at which at least a portion of the saturated chlorinated impurity may be converted to a second saturated derivative selected from the group consisting of a saturated hydrodechlorinated derivative and a saturated fluorinated derivative may be from about 200° C. to about 350° C. Depending on the reactivity of the olefinic impurity and saturated chlorinated impurity, addition of hydrogen fluoride to olefins and fluorine-for-chlorine halogen exchange by reaction with hydrogen fluoride in the presence of catalyst will take place throughout this temperature range. For thermally unstable hydrofluoropropanes which can readily dissociate hydrogen fluoride at elevated temperatures, such as HFC-245fa, it is preferable to carry out the present process at the minimal temperature required to substantially remove the impurities. Operating the present process at higher temperatures than required to substantially remove the impurities may reduce the effectiveness of the process and result in formation of further impurities and hydrofluoropropane yield loss.

The contacting step of the present process may be conducted in a reaction zone in which said contacting occurs in the liquid phase or in the vapor phase. The reaction zone may comprise, for example, a stirred tank reactor or a tubular reactor using well-known chemical engineering practices including batch, semi-batch, or continuous operations. The contacting step of the present process is preferably carried out in the vapor phase.

The present invention is a process for purifying a hydrofluoropropane of olefinic and saturated chlorinated impurities and results in hydrofluoropropane containing reduced amounts of, or substantially free of, said impurities. By "substantially free" is meant that the contacting step of the present process results in a second mixture comprising hydrofluoropropane and less than about 1,000 ppm of each of the olefinic impurity and the saturated chlorinated impurity. By following the teachings of the present description, the contacting step of the present process may result in a second mixture comprising hydrofluoropropane and less than about 500 ppm of each of the olefinic impurity and the saturated chlorinated impurity. By following the preferred teachings of the present description, the contacting step of the present process may result in a second mixture comprising hydrofluoropropane and less than about 100 ppm of each of the olefinic impurity and the saturated chlorinated impurity.

Following the contacting step of the present invention, the hydrofluoropropanes of the second mixture may be recovered and further purified by known processes. For example, the present process may further comprise distilling the second mixture and thereby separating hydrofluoropropane from unreacted hydrogen and hydrogen fluoride as well as from at least one of the first saturated derivatives and second saturated derivatives formed from the impurities, and recovering the hydrofluoropropane substantially free of at least one of the first saturated derivatives and second saturated derivatives.

Without further elaboration, it is believed that one of average skill in this field can, using the description herein, utilize the present invention to its fullest extent. The following specific embodiments are, therefore, to be construed as merely illustrative, and do not constrain the remainder of the disclosure in any way whatsoever.

EXAMPLES

| LEGEND | |
|---|---|
| 225da is $CF_3CHClCClF_2$ | 226da is $CF_3CHClCF_3$ |
| 235fa is $CF_3CH_2CClF_2$ | 235da is $CF_3CHClCHF_2$ |
| 236ea is $CF_3CHFCHF_2$ | 236fa is $CF_3CH_2CF_3$ |
| 245fa is $CF_3CH_2CHF_2$ | 253fb is $CF_3CH_2CH_2Cl$ |
| 254fb is $CF_3CH_2CH_2F$ | 263fb is $CF_3CH_2CH_3$ |
| 347 is $C_4H_3F_7$ | 356mff is $CF_3CH_2CH_2CF_3$ |
| 1214 is $C_4Cl_2F_4$ | 1224 is $C_4HClF_4$ |
| 1215xc is $CF_3CCl=CF_2$ | 1225zc is $CF_3CH=CF_2$ |
| 1233 is $C_3H_2ClF_3$ | 1234ze is E- or Z-$CHF=CHCF_3$ |
| 1243 is $C_3H_3F_3$ | 1327 is $C_4HF_7$ |
| 30 is $CH_2Cl_2$ | CT is contact time |

General Procedure for Hydrogenation Reactions

The following general procedure was followed in the hydrogenation of mixtures of fluoropropanes and fluoropropenes.

The catalyst (5 cc) was placed in a ½" (1.27 cm) diameter Inconel™ nickel alloy reactor tube heated in a fluidized sand bath. Any activation of the catalyst is indicated in the examples. Prior to beginning an experiment, the reactor was then heated from about 150° C. to about 200° C. in a flow of hydrogen (15 cc/min, $2.5 \times 10^{-7}$ m³/s) for 0.5 hour to 1 hour. The temperature of the reactor was then adjusted to the desired starting point and the fluorocarbon mixture was then fed to the reactor as a vapor via a flow controller. The contact time in the reactor was typically 15 seconds. All reactions were conducted at a nominal pressure of one atmosphere.

General Procedure for Fluorocarbon Product Analysis

The following general procedure is illustrative of the method used for analyzing the products of fluorocarbon reactions. Part of the total reactor effluent was sampled on-line for organic product analysis using a gas chromatograph equipped a with mass selective detector (GC-MS). The gas chromatography was accomplished with a 20 ft. (6.1 m) long×⅛ in. (0.32 cm) diameter tubing containing Krytox® perfluorinated polyether on an inert carbon support. The helium flow was 30 mL/min ($5.0 \times 10^{-7}$ m$^3$/s). Gas chromatographic conditions were 60° C. for an initial hold period of three minutes followed by temperature programming to 200° C. at a rate of 6° C./minute. For experiments involving mixtures containing HFC-245fa, the preferred GC column was a 105 meter dimethylpolysiloxane-coated capillary column. The flow rate in the capillary column was 1.6 sccm ($2.7 \times 10^{-8}$ m$^3$/s) and the chromatographic conditions were were 60° C. for an initial hold period of ten minutes followed by temperature programming to 200° C. at a rate of 6° C./minute. Minor by-products whose individual concentrations were less than 100 ppm of the total product are not listed.

The bulk of the reactor effluent containing organic products and also inorganic acids such as HCl and HF was treated with aqueous caustic prior to disposal.

Comparative Example 1

Hydrogenation of a Mixture of HFC-236fa, HFC-1225zc and CFC-1215xc

A commercial sample of 0.5% palladium supported on aluminum oxide (5.24 g, 5 mL, ¹⁄₁₆ inch (0.16 cm) extrudates) was placed in a reactor tube heated in a fluidized sand bath. The catalyst had been previously activated by purging with nitrogen at 300° C. followed by hydrogen treatment at 150° C. to 200° C., and finally fluorination with an HF/N$_2$ mixture at temperatures up to 400° C. A mixture comprising HFC-236fa (89.4 GC area %), HFC-1225zc (7.9 GC area %), CFC-1215xc (2.5 GC area %), methylene chloride (0.01%), HFC-143a (0.03%), HFC-1327 (0.03%), and HCFC-226da (0.21%) was fed to the reactor along with hydrogen. The mole ratio of hydrogen to the fluorocarbon mixture was 1:1 and the contact time was 15 seconds. GC-MS analysis of the reactor effluent at 150° C., 200° C., and 250° C. are given below. Also shown is the GC-MS analysis of the reactor effluent at 200° C. when the mole ratio of hydrogen to the fluorocarbon mixture was 2:1.

| | GC Area % | | | |
|---|---|---|---|---|
| Component | 150° C. | 200° C. | 250° C. | 200° C. (2:1) |
| HFC-236fa | 92.2 | 91.2 | 95.2 | 92.0 |
| HFC-1225zc | 6.5 | 5.6 | 0.7 | 0.4 |
| CFC-1215xc | 0.4 | 0.2 | 0.2 | — |
| HFC-263fb | — | — | 2.7 | 0.07 |
| HCFC-235da | 0.4 | 0.3 | 0.1 | 0.08 |
| HFC-245fa | 0.2 | 2.3 | trace | 6.5 |
| HFC-1234ze | — | — | 0.3 | — |
| HFC-1243 | — | — | 0.04 | — |
| HFC-1327 | 0.01 | 0.01 | 0.02 | — |
| HFC-347 | 0.02 | 0.02 | 0.02 | 0.03 |

| | GC Area % | | | |
|---|---|---|---|---|
| Component | 150° C. | 200° C. | 250° C. | 200° C. (2:1) |
| HCFC-1224 | 0.01 | 0.01 | 0.01 | — |
| HCFC-226da | 0.2 | 0.2 | 0.2 | 0.1 |
| HCC-30 | 0.02 | 0.01 | — | 0.01 |
| Propane | — | 0.01 | 0.31 | 0.01 |
| Ethane | — | 0.01 | 0.11 | 0.02 |
| Methane | — | 0.02 | 0.07 | 0.03 |

Comparative Example 2

Hydrogenation of a Mixture of HFC-236fa, HFC-1225zc and CFC-1215xc

A palladium-doped chromium oxide catalyst (Cr/Pd ratio=98/2; 6.99 g, 5 mL, −12 to +20 mesh, (1.68 to 0.84 mm)) was prepared by treating a solution of 784.30 g Cr(NO$_3$)$_3$[9(H$_2$O)] (1.96 mole) and 9.34 g Pd(NO$_3$)$_2$[2 (H$_2$O)] (0.04 mole) dissolved in 2 L of deionized water with 950 mL of 7.4M aqueous ammonia. The mixture was stirred overnight at room temperature and then evaporated to dryness in air at 110–120° C. and held at that temperature overnight. The dried catalyst was ground to a powder and then calcined in air at 400° C. for 24 hours. The resulting catalyst was purged with nitrogen and heated under H$_2$ to a temperature of 275° C. and then fluorinated with an HF/N$_2$ mixture at temperatures up to 400° C. The catalyst was placed in the reactor tube and pre-reduced with hydrogen at 150° C. A mixture comprising HFC-236fa (89.4 GC area %), HFC-1225zc (7.9 GC area %), CFC-1215xc (2.5 GC area %), methylene chloride (0.01%), HFC-143a (0.03%), HFC-1327 (0.03%), and HCFC-226da (0.21%) was fed to the reactor along with hydrogen; the contact time was 15 seconds. GC-MS analysis of the reactor effluent at 125° C. and 200° C. (mole ratio of hydrogen to fluorocarbon mixture=2:1) and at 150° C. and 250° C. (mole ratio of hydrogen to fluorocarbon mixture=1:1) are given below.

| | GC Area % | | | |
|---|---|---|---|---|
| Component | 125° C. (2:1) | 200° C. (2:1) | 150° C. (1:1) | 250° C. (1:1) |
| HFC-236fa | 93.1 | 91.7 | 92.3 | 88.2 |
| HFC-1225zc | — | — | 0.06 | 0.02 |
| CFC-1215xc | — | — | 0.01 | — |
| HFC-263fb | 0.03 | 4.4 | 0.2 | 3.8 |
| HCFC-235da | 0.6 | 0.1 | 0.9 | 0.01 |
| HFC-245fa | 5.9 | 2.6 | 5.9 | — |
| HFC-347 | 0.03 | 0.03 | 0.03 | 0.03 |
| HCFC-226da | 0.2 | 0.07 | 0.2 | — |
| HCFC-253fb | 0.06 | 0.7 | 0.4 | 0.01 |
| HCC-30 | 0.02 | — | — | — |
| Propane | — | 0.2 | — | 7.6 |
| Ethane | — | 0.03 | — | 0.2 |
| Methane | — | 0.07 | 0.01 | 0.1 |

Example 1

Hydrogenation and Fluorination of a Mixture of HFC-236fa, HFC-1225zc, and CFC-1215xc Comparative example 1 was repeated but with anhydrous hydrogen fluoride co-fed to the reactor. The mole ratio of hydrogen, fluorocarbon mixture, and HF was 2:1:2; the contact time was 10 seconds. The GC-MS analysis of the reactor effluent at 175° C. and 250° C. are given below.

| Component | GC Area % | |
|---|---|---|
| | 175° C. | 250° C. |
| HFC-236fa | 92.9 | 97.0 |
| HFC-1225zc | 0.6 | 0.3 |
| HFC-263fb | — | 0.4 |
| HCFC-235da | 0.05 | 0.02 |
| HFC-245fa | 5.7 | 2.0 |
| HFC-254fb | 0.5 | — |
| HFC-1234ze | — | 0.01 |
| HFC-347 | 0.03 | 0.03 |
| HCFC-226da | 0.2 | 0.03 |
| HCC-30 | 0.01 | — |
| Propane | — | 0.02 |
| Ethane | — | 0.03 |
| Methane | — | 0.09 |

Example 2

Hydrogenation and Fluorination of a Mixture of HFC-236fa, HFC-1225zc, and CFC-1215xc Comparative example 2 was repeated but with anhydrous hydrogen fluoride co-fed to the reactor. The mole ratio of hydrogen, fluorocarbon mixture, and HF was 2:1:2; the contact time was 10 seconds. The GC-MS analysis of the reactor effluent at 200° C. and 250° C. are given below.

| Component | GC Area % | |
|---|---|---|
| | 200° C. | 250° C. |
| HFC-236fa | 94.1 | 92.5 |
| HFC-263fb | 0.5 | 2.2 |
| HCFC-235da | 0.03 | — |
| HFC-245fa | 5.1 | 0.6 |
| HFC-347 | 0.03 | 0.03 |
| HCFC-226da | 0.02 | — |
| HCFC-253fb | 0.2 | 0.04 |
| Propane | 0.02 | 4.4 |
| Ethane | 0.01 | 0.1 |
| Methane | 0.06 | 0.1 |

Comparative Example 3

Fluorination of a Mixture of HFC-236fa, HFC-1225zc, and CFC-1215xc

Example 1 was repeated but without hydrogen. The mole ratio of fluorocarbon mixture to HF was 1:2; the contact time was 15 seconds. The GC-MS analysis of the reactor effluent at 300° C. is given below.

| Component | GC Area % 300° C. |
|---|---|
| HFC-236fa | 97.0 |
| HFC-1225zc | 0.2 |
| CFC-1215xc | 1.1 |
| HFC-1327 | 0.03 |
| HCFC-1224 | 0.01 |
| HCFC-226da | 1.7 |

Comparative Example 4

Fluorination of a Mixture of HFC-236fa HFC-1225zc, and CFC-1215xc

Example 2 was repeated but without hydrogen. The mole ratio of fluorocarbon mixture to HF was 1:2; the contact time was 15 seconds. The GC-MS analysis of the reactor effluent at 300° C. is given below.

| Component | GC Area % 300° C. |
|---|---|
| HFC-236fa | 97.4 |
| HFC-1225zc | 0.1 |
| CFC-1215xc | 0.01 |
| HFC-1327 | 0.02 |
| HCFC-226da | 2.3 |

Comparative Example 5

Hydrogenation of a Mixture of HFC-236fa, HFC-1225zc, and CFC-1215xc

A catalyst comprising 0.8% palladium and 1.2% gold supported on carbon catalyst (1.9 g, 5 mL, 4 to 8 mesh, (4.75 to 2.36 mm)), prepared as described in U.S. Pat. No. 5,447,698, was placed in the reactor tube. The catalyst was pre-treated with hydrogen at temperatures of to 200° C. A mixture comprising HFC-236fa (89.4 GC area %), HFC-1225zc (7.9 GC area %), CFC-1215xc (2.5 GC area %), methylene chloride (0.01%), HFC-143a (0.03%), HFC-1327 (0.03%), and HCFC-226da (0.21%) was fed to the reactor along with hydrogen; the contact time was 15 seconds. GC-MS analysis of the reactor effluent at 125° C. and 200° C. (mole ratio of hydrogen to fluorocarbon mixture=1:1) and at 250° C. (mole ratio of hydrogen to fluorocarbon mixture=2:1) are given below.

| Component | GC Area % | | |
|---|---|---|---|
| | 125° C. (1:1) | 200° C. (1:1) | 250° C. (2:1) |
| HFC-236fa | 93.4 | 94.1 | 94.1 |
| HFC-263fb | — | 0.01 | 0.02 |
| HCFC-235da | 0.2 | — | — |
| HFC-245fa | 6.1 | 5.7 | 5.6 |
| HCFC-226da | 0.2 | — | — |
| HCFC-253fb | 0.01 | 0.02 | 0.03 |
| HCC-30 | 0.02 | — | — |
| HFC-347 | 0.03 | 0.03 | 0.03 |
| Methane | — | 0.03 | 0.04 |

Example 3

Hydrogenation and Fluorination of a Mixture of HFC-236fa, HFC-1225zc, and CFC-1215xc Comparative example 5 was repeated but with anhydrous hydrogen fluoride co-fed to the reactor. A mixture comprising HFC-236fa (93.0 GC area %), HFC-1225zc (4.1 GC area %), CFC-1215xc (2.6 GC area %), methylene chloride (0.01%), HFC-143a (0.01%), HFC-1327 (0.04%), HCFC-1224 (0.01%), methane (0.01%), and HCFC-226da (0.29%) was fed to the reactor along with hydrogen and hydrogen fluoride; the contact time was 10 seconds. GC-MS analyses of the reactor effluent at 125° C. and 200° C. (mole ratio of hydrogen to fluorocarbon mixture to HF=1:1:2) and at 250° C. (mole ratio of hydrogen to fluorocarbon mixture to HF=2:1:2) are given below.

| | GC Area % | | |
|---|---|---|---|
| Component | 125° C. (1:1:2) | 200° C. (1:1:2) | 250° C. (2:1:2) |
| HFC-236fa | 94.9 | 95.3 | 95.4 |
| HFC-1225zc | 0.03 | 0.01 | — |
| HFC-254fb | 0.03 | 0.04 | 0.09 |
| HFC-263fb | 0.01 | 0.01 | 0.02 |
| HCFC-235da | 0.2 | 0.01 | — |
| HFC-245fa | 4.5 | 4.6 | 4.4 |
| HFC-347 | 0.04 | 0.04 | 0.04 |
| HCFC-226da | 0.3 | 0.02 | — |
| HCC-30 | 0.02 | 0.01 | — |
| Methane | 0.01 | 0.02 | 0.05 |

Comparative Example 6

Hydrogenation of a Mixture of HFC-245fa, HFC-1225zc, and HFC-1234ze

The palladium-doped chromium oxide catalyst (6.89 g) used in comparative example 4 was placed in the reactor tube heated in a fluidized sand bath. A mixture comprising HFC-245fa (91.9 GC area %), HFC-1225zc (0.34 GC area %), E- or Z-HFC-1234ze (5.9 GC area %), HFC-236fa (0.3 GC area %), HFC-236ea (1.6 GC area %), and HCFC-1233 (0.01%) was fed to the reactor along with hydrogen; the contact time was 15 seconds. GC-MS analysis of the reactor effluent at 100° C. and 200° C. (mole ratio of hydrogen to fluorocarbon mixture=1:1) and at 200° C. (mole ratio of hydrogen to fluorocarbon mixture=2:1) are given below.

| | GC Area % | | |
|---|---|---|---|
| Component | 100° C. (1:1) | 200° C. (1:1) | 200° C. (2:1) |
| HFC-245fa | 93.9 | 87.2 | 74.5 |
| HFC-254fb | 4.3 | 2.3 | 2.6 |
| HFC-1234ze (E/Z) | — | 0.06 | 0.2 |
| HFC-263fb | — | 8.5 | 20.6 |
| HFC-236fa | 0.3 | 0.3 | 0.2 |
| HFC-236ea | 1.4 | 1.3 | 1.3 |
| Ethane | — | 0.2 | 0.4 |
| Methane | — | 0.09 | 0.08 |

Comparative Example 7

Hydrogenation of a Mixture of HFC-245fa, HFC-1225zc, and HFC-1234ze

The 0.8% palladium/1.2% gold supported on carbon catalyst (1.97 g) used in comparative example 5 was placed in the reactor tube heated in a fluidized sand bath. A mixture comprising HFC-245fa (86.2 GC area %), HFC-1225zc (0.9 GC area %), E- or Z-HFC-1234ze (10.8 GC area %), HFC-236fa (0.4 GC area %), HFC-236ea (1.7 GC area %), and HCFC-1233 (0.01%) was fed to the reactor along with hydrogen in a molar ratio of 1:1; the contact time was 15 seconds. The GC-MS analysis of the reactor effluent at 100° C. is given below.

| Component | GC Area % 100° C. (1:1) |
|---|---|
| HFC-245fa | 89.2 |
| HFC-254fb | 8.8 |
| HFC-236fa | 0.4 |
| HFC-236ea | 1.5 |
| Methane | 0.01 |

Comparative Example 8

Hydrogenation of a Mixture of HFC-245fa, HFC-1225zc, and HFC-1234ze

A mixture comprising HFC-245fa (91.9 GC area %), HFC-1225zc (0.3 GC area %), E- or Z-HFC-1234ze (5.9 GC area %), HFC-236fa (0.3 GC area %), HFC-236ea (1.6 GC area %), and HCFC-1233 (0.01%) was passed over the 0.8% palladium/1.2% gold supported on carbon catalyst used in comparative example 7. The molar ratio of hydrogen to fluorocarbon was 2:1 and the contact time was 15 seconds. The GC-MS analysis of the reactor effluent at 200° C. is given below.

| Component | GC Area % 200° C. (2:1) |
|---|---|
| HFC-245fa | 92.0 |
| HFC-254fb | 6.1 |
| HFC-236fa | 0.4 |
| HFC-236ea | 1.5 |
| Methane | 0.01 |

What is claimed is:

1. A process for purifying a hydrofluoropropane comprising:

contacting a first mixture comprising a hydrofluoropropane, an olefinic impurity and a saturated chlorinated impurity with hydrogen and hydrogen fluoride concurrently in the presence of a bifunctional catalyst, whereby said olefinic impurity is converted to at least one first saturated derivative selected from the group consisting of a saturated hydrogenated derivative of said olefinic impurity and a saturated hydrofluorinated derivative of said olefinic impurity, and whereby said saturated chlorinated impurity is converted to at least one second saturated derivative selected from the group consisting of a saturated hydrodechlorinated derivative of said saturated chlorinated impurity and a saturated fluorinated derivative of said saturated chlorinated impurity, to form a second mixture comprising hydrofluoropropane substantially free of said olefinic impurity and said saturated chlorinated impurity, and recovering said second mixture.

2. The process of claim 1 further comprising distilling said second mixture thereby separating said hydrofluoropropane from at least one of said first saturated derivative and said second saturated derivative, and recovering said hydrofluoropropane substantially free of at least one of said first saturated derivative and said second saturated derivative.

3. The process of claim 1 wherein: said hydrofluoropropane is represented by the formula $C_3H_mF_{8-m}$, wherein m is an integer from 1 to 7; said olefinic impurity is represented by the formula $C_nH_pCl_qF_r$, wherein n is an integer from 2 to 4, p is an integer from 0 to 8, q is an integer from 0 to 2, r is an integer from 0 to 8, and p+q+r=2n; and said saturated chlorinated impurity is represented by the formula $C_sH_tCl_uF_v$, wherein s is an integer from 1 to 4, t is an integer from 0 to 9, u is an integer from 1 to 3, v is an integer from 0 to 9, and t+u+v=2s+2.

4. The process of claim 1 wherein said contacting is carried out in the vapor phase at a temperature of from about 100° C. to about 400° C.

5. The process of claim 1 wherein said bifunctional catalyst comprises a transition metal supported on a fluorination catalyst, wherein said transition metal is selected from the group consisting of palladium, platinum and gold.

6. The process of claim 5 wherein said fluorination catalyst is selected from the group consisting of carbon, fluorinated aluminum(III) oxide, and fluorinated chromium (III) oxide.

7. The process of claim 1 wherein said bifunctional catalyst comprises an alloy of gold and palladium supported on carbon.

8. The process of claim 1 wherein said second mixture contains less than about 500 ppm of each of said olefinic impurity and said saturated chlorinated impurity.

9. The process of claim 1 wherein said second mixture contains less than about 100 ppm of each of said olefinic impurity and said saturated chlorinated impurity.

10. A process for reducing the concentration of olefinic impurity and saturated chlorinated impurity in a first mixture comprising hydrofluoropropane, olefinic impurity and saturated chlorinated impurity, comprising:

contacting said first mixture with hydrogen and hydrogen fluoride concurrently in the presence of a bifunctional catalyst, whereby at least a portion of said olefinic impurity is converted to at least one first saturated derivative selected from the group consisting of a saturated hydrogenated derivative of said olefinic impurity and a saturated hydrofluorinated derivative of said olefinic impurity, and whereby at least a portion of said saturated chlorinated impurity is converted to at least one second saturated derivative selected from the group consisting of a saturated hydrodechlorinated derivative of said saturated chlorinated impurity and a saturated fluorinated derivative of said saturated chlorinated impurity, to form a second mixture comprising hydrofluoropropane wherein the concentration of said olefinic impurity and said saturated chlorinated impurity is reduced from the concentration of said olefinic impurity and said saturated chlorinated impurity contained in said first mixture, and recovering said second mixture.

* * * * *